(12) United States Patent
Kumar et al.

(10) Patent No.: US 6,803,468 B2
(45) Date of Patent: Oct. 12, 2004

(54) PROCESS FOR THE SYNTHESIS OF N-(5-METHYLNICONTINOYL)-4 HYDROXYPIPERIDINE, A KEY INTERMEDIATE OF RUPATADINE

(75) Inventors: Yatendra Kumar, Haryana (IN); Mohan Prasad, Haryana (IN); Shallendra Kumar Singh, Haryana (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 10/363,371

(22) PCT Filed: Aug. 28, 2001

(86) PCT No.: PCT/IB01/01555

§ 371 (c)(1),
(2), (4) Date: Jun. 20, 2003

(87) PCT Pub. No.: WO02/18366

PCT Pub. Date: Mar. 7, 2002

(65) Prior Publication Data

US 2004/0044216 A1 Mar. 4, 2004

(30) Foreign Application Priority Data

Aug. 29, 2000 (IN) .................................... 781/DEL/2000

(51) Int. Cl.[7] ...................... C07C 211/68; C07C 211/22

(52) U.S. Cl. ...................... 546/193; 546/193; 546/221
(58) Field of Search .................. 546/193, 221

(56) References Cited

U.S. PATENT DOCUMENTS 5,407,941 A    4/1995   Carceller et al. ........... 514/290

FOREIGN PATENT DOCUMENTS

| EP | 577957 | 1/1995 | ......... C07D/401/00 |
| ES | 2042421 | 12/1993 | ......... C07D/401/17 |
| ES | 2120899 | 11/1998 | ......... C07D/401/14 |

OTHER PUBLICATIONS

Mehrsheikh et al, Jol. Lab. Cps. & Radiopham. vol. 29 No. 1 pp 9–13 (1991) abstract.*

* cited by examiner

*Primary Examiner*—Rita Desai
*Assistant Examiner*—Raymond Covington
(74) *Attorney, Agent, or Firm*—Jayadeep R. Deshmukh, Esq.; George E. Heibel, Esq.; William D. Hare, Esq.

(57) ABSTRACT

The present invention relates to an improved and industrially advantageous process for the preparation of N-(5-methylnicotinoyl)-4-hydroxypiperidine of Formula I, as shown in the accompanied drawings. This compound is a key intermediate for the synthesis of rupatadine, a potent dual antagonist of histamine and platelet-activating factor (PAF).

26 Claims, No Drawings

PROCESS FOR THE SYNTHESIS OF N-(5-METHYLNICONTINOYL)-4 HYDROXYPIPERIDINE, A KEY INTERMEDIATE OF RUPATADINE

FIELD OF THE INVENTION

The present invention relates to an improved and industrially advantageous process for the preparation of N-(5-methylnicotinoyl)-4-hydroxypiperidine of Formula I:

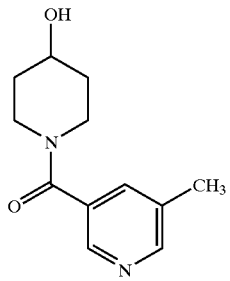

FORMULA I

This compound is a key intermediate for the synthesis of rupatadine, a potent dual antagonist of histamine and platelet-activating factor (PAF).

BACKGROUND OF THE INVENTION

Chemically, rupatadine is 8-chloro-11-[1-[(5-methyl-3-pyridyl)methyl]-piperidin-4-ylidene]-6,11-dihydro-5H-benzo[5,6]cyclohepta[1,2-b]pyridine having Formula II

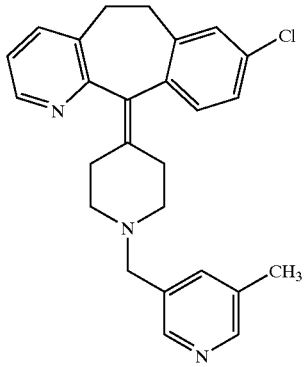

FORMULA II

This compound is known in the literature as UR-12592 and is known from Spanish Patent No. 2,042,421 (U.S. Pat. No. 5,407,941 and European Patent No. 577957 are its equivalents in United States and Europe, respectively) assigned to Uriach of Spain. Rupatadine fumarate is a potent dual antagonist of histamine and PAF, with good activity and long duration of action when given by oral route. General pharmacology and toxicity studies reveal a good safety profile. Although compounds with either potent antihistamine properties or PAF antagonist activity are available, rupatadine fumarate possesses a unique profile as it combines both activities with a high level of potency. This dual activity is an advantage over other drugs in the treatment of clinical conditions such as allergic rhinitis, urticaria, atopic eczema or asthma.

A previously known method for the synthesis of the intermediate N-(5-methylnicotinoyl)-4-hydroxy piperidine of Formula I was reported in Spanish Patent No. 2,120,899 assigned to Uriach which involves the reaction of 5-methylnicotinic acid of Formula III

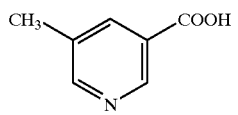

FORMULA III in the presence of 1,3-dicyclohexylcarbodiimide (DCC) and 1-hydroxybenzotriazole hydrate (HOBT) for 18 hours at room temperature.

The above mentioned method described in the prior art for the manufacture of the desired compound of Formula I suffers from the following limitations:

The process requires commercially limited available and costly raw materials such as 1,3-dicyclohexylcarbodiimide (DCC) and 1-hydroxybenzotriazole hydrate (HOBT).

The process generates a lot of effluent waste such as dicyclohexyl urea and hence is not eco-friendly.

Dicyclohexyl urea generated during the reaction can not be easily removed during the work up at large scale and repeated purification of crude and impure N-(5-methylnicotinoyl)-4-hydroxypiperidine leads to overall loss of yield and makes this process less economically viable.

In order to obtain rupatadine in pure form it is necessary to employ a starting material of suitable purity.

SUMMARY OF THE INVENTION

It is an object of the present invention to solve the problems, associated with the prior art and to provide an efficient method for the preparation of N-(5-methylnicotinoyl)-4-hydroxypiperidine of Formula I (as shown in the accompanied drawings). The product obtained by the process of the present invention would be highly useful as a starting material for the preparation of pure rupatadine.

More particularly, the present invention relates to a process for the preparation of N-(5-methylnicotinoyl)-4-hydroxypiperidine of Formula I (as shown in the accompanied drawings) comprising reacting 5-methylnicotinic acid of Formula III with alkyl chloroformate or pivaloyl chloride to give mixed anhydride of Formula IV

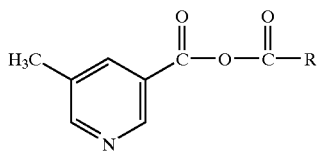

FORMULA IV wherein R is alkyl or substituted alkyl preferably methyl, ethyl or tertiary butyl, in a suitable solvent in the presence of an organic base, which on further reaction with 4-hydroxypiperidine of Formula V

FORMULA V

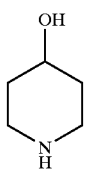

affords the desired product of Formula I.

The alkyl chloroformate is selected from the group consisting of methyl chloroformate, ethyl chloroformate and butyl chloroformate, preferably methyl chloroformate. The alkyl chloroformate or pivaloyl chloride is suitably used in an amount of 1.0 to 2.0 molar equivalents of compound of Formula II, and preferably in an amount of 1.1 to 1.5 molar equivalents.

The term "suitable solvent" includes chlorinated solvents, aromatic solvents, ethers, esters and mixture(s) thereof. Preferably, the solvent may be selected from the group consisting of dichloromethane, chloroform, toluene, tetrahydrofuran, ethyl acetate and mixture(s) thereof. The solvent is suitably used in an amount of 5 to 20 times of weight of the compound of Formula II, and preferably, in an amount 5 to 10 times.

The suitable organic base is selected from the group comprising triethylamine, trimethylamine, picolines, pyridine, pyridine derivatives, morpholine and morpholine derivatives. The organic base is suitably used in an amount of 1.0 to 2.0 molar equivalents of the compound of Formula III and preferably in an amount of 1.1 to 1.5 molar equivalents.

The reaction of mixed anhydride of Formula IV (wherein R is same as defined earlier) with 4-hydroxy peperidine of Formula V is carried out at a selected temperature range of −40° C. to 10° C. preferably at −15 to 10° C. during a period of 3 hours to several hours. The desired compound N-(5-methylnicotinoyl)-4-hydroxypiperidine of Formula I is isolated by suitable aqueous basic work up.

Suitable aqueous basic work-up involves the adjustment of pH with a base and extraction with organic solvents. Bases may include sodium or potassium hydroxide, sodium hydroxide being the preferred base.

Any organic solvent may be used for extraction and such solvents are known to a person of ordinary skill in the art and include water-immiscible and partially miscible solvents, such as chloroform, dichloromethane, 1,2-dichloroethane, hexanes, cyclohexane, toluene, methyl or ethyl acetate and the like.

The product may be obtained by reducing the volume of organic solvent containing the desired compound by evaporation or evaporation under vacuum, adding a miscible polar solvent and precipitating the desired product by addition of an anti-solvent. Polar solvent may be selected from a group consisting of a lower alkanol, ketones, esters and mixtures thereof. Preferably, the solvent may be selected from the group consisting of methanol, ethanol, acetone, ethyl acetate and mixture(s) thereof.

Suitable anti-solvents include alkanes, mixture of alkanes, such as hexane, cyclohexane or cyclopentane or ethers, such as isopropylether, or aromatic hydrocarbons, such as benzene or toluene. The polar solvent and an anti-solvent should be at least partially miscible and preferably completely miscible.

DETAILED DESCRIPTION OF THE INVENTION

In the following section several preferred embodiments are described by way of examples to illustrate the process of the invention. However, these are not intended in any way to limit the scope of the invention.

Preparation of N-(5-Methylnicotinoyl)-4-Hydroxy Piperidine

EXAMPLE 1

To a suspension of 5-methyl nicotinic acid (25 gm) in methylene chloride (150 ml) was added triethylamine (20.2 gm) at 0–5° C. It was stirred for about 10 minutes at 0–5° C. and then cooled it to −15° C. Pyridine hydrobromide (0.5 gm) and pivaloyl chloride (23.1 gm) were added and the reaction mixture was stirred for about 1.5 hours at −5° C. to −10° C. A solution of 4-hydroxypiperidine (23 gm) in methylene chloride (100 ml) was added to it at −5° C. to −10° C. The reaction mixture was further stirred for 3 hours at 0 to 5° C. The reaction mixture was worked up by adding water (50 ml) to it. It was stirred for 5 minutes and the organic layer was separated. It was concentrated under vacuum and pH of the residue was adjusted to about 7.8 with 2N aqueous sodium hydroxide and extracted the desired compound with methylene chloride (3×90 ml). The solvent from the combined extract was removed under vacuum to afford crude N-(5-methylnicotinoyl)-4-hydroxypiperidine which was crystallized from a mixture of ethyl acetate and hexane to give pure white (purity by HPLC 99%) compound (30.5 gm, 76.2%).

EXAMPLE 2

5-Methylnicotinic acid (5 gm) was suspended in methylene chloride (30 ml) and cooled it to 0 to 5° C. Added triethylamine (4.42 gm) to it and cooled the reaction mixture to −35° C. to −40° C. To it was added a mixture of N-methyl morpholine (10 mg) and ethyl chloroformate (4.54 gm) at −40° C. Reaction mixture thus obtained was stirred at −35° C. to −40° C. for about 1.5 hrs. Added a solution of 4-hydroxy piperidine (3.7 gm) in methylene chloride (20 ml) at −40° C. to −35° C. during a period of 10 minutes. Stirred the reaction mixture for about 4 hours at −20° C. to −15° C., added water (930 ml) to it and the two layers were separated. Concentrated the organic layer under vacuum, and pH of the residue was adjusted to 7.8 with 2N sodium hydroxide. Extracted the desired compound with methylene chloride (3×30 ml) and the combined extract was subjected to vacuum distillation to remove the solvent completely. The crude product thus obtained was crystallized from ethyl acetate and hexane to give 5.9 gm (73.7%) of the pure product (Purity by HPLC 98.8%).

EXAMPLE 3

5-Methyl nicotinic acid (10 gm) was suspended in methylene chloride (60 ml) and to it was added N-methyl morpholine (11 gm) at 0° C. Stirred it for about 5 minutes at 0–5° C. and then it was cooled to −15° C. Pyridine hydrobromide (0.2 gm) and pivaloyl chloride (9.67 gm) were added at −15° C. Reaction mixture thus obtained was stirred at −15° C. to −10° C. for about 2 hours. A solution of 4-hydroxypiperidne (9.2 gm) in methylene chloride (40 ml) was added to the reaction mixture at −10° C. to −5° C. during a period of 20 minutes. The reaction mixture thus obtained was stirred at 0 to 5° C. for about 3 hours and water (20 ml) was added to the reaction mixture. Two layers were separated, organic layer was concentrated under vacuum and pH of the residue was adjusted to 7.8 with 2N aqueous sodium hydroxide and it was then extracted with methylene chloride (3×30 ml). Concentrated the methylene chloride layer under vacuum and the crude product thus obtained was crystallized from ethyl acetate and hexane to afford a white solid (11.5 gm, 71%; Purity by HPLC-98.9%).

EXAMPLE 4

Methyl nicotinic acid (10 gm) was suspended in methylene chloride (60 ml) and cooled to 0° C. Added pyridine (11.5 gm) to it and stirred for about 10 minutes at 0 to 5° C. Cooled it to about −20° C. and added pyridine hydrobromide (0.2 gm) followed by addition of pivaloyl chloride (9.67 gm) at −20° C. Reaction mixture thus obtained was stirred at −15° C. to −20° C. for about 2 hours. A solution of 4-hydroxypiperidine (9.2 gm) in methylene chloride (40 ml) was added to the reaction mixture at −10° C. to −15° C. Reaction mixture thus obtained was stirred at 5–10° C. for about 3 hours. Added water (20 ml), stirred for 5 minutes at 15–20° C. and layers were separated. Organic layer was concentrated under vacuum and pH of the residue was adjusted to 8.2 with 2N aqueous sodium hydroxide. It was extracted with methylene chloride and the methylene chloride layer was concentrated to give crude N-(5-methylnicotinoyl)-4-hydroxypiperidine. The crude product thus obtained was crystallized from ethyl acetate and hexane to give 8 gm (yield 73%) of the pure product (Purity by HPLC 99.1%).

While the present invention has been described in terms of its specific embodiments, certain modifications and equivalents will be apparent to those skilled in the art and are intended to be included within the scope of the present invention.

We claim:

1. A process for the preparation of N-(5-methylnicotinoyl)-4-hydroxy piperidine of Formula I

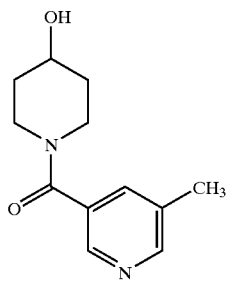

FORMULA I comprising reacting 5-methylnicotinic acid of Formula III

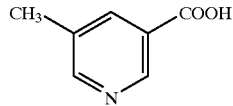

FORMULA III with alkyl chloroformate or pivaloyl chloride to give mixed anhydride of Formula IV

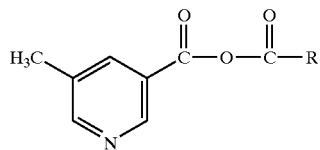

FORMULA IV wherein R is alkyl or substituted alkyl preferably methyl, ethyl or tertiary butyl, in a suitable solvent in the presence of an organic base, and further reacting the mixed anhydride of Formula IV with 4-hydroxypiperidine of Formula V

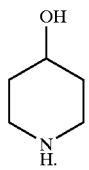

FORMULA V

2. The process of claim 1, wherein the alkyl chloroformate is selected from the group consisting of methyl chloroformate, ethyl chloroformate and butyl chloroformate.

3. The process of claim 2, wherein the alkyl chloroformate is methyl chloroformate.

4. The process of claim 1 wherein the suitable solvent is selected from the group consisting of chlorinated solvents, aromatic solvents, ethers, esters and mixture(s) thereof.

5. The process of claim 4 wherein the solvent is selected from the group consisting of dichloromethane, chloroform, toluene, tetrahydrofuran, ethyl acetate and mixture(s) thereof.

6. The process of claim 1 wherein organic base is selected from the group consisting of trimethylamine, triethylamine, picolines, pyridine, pyridine derivatives, morpholine, morpholine derivatives and mixture(s) thereof.

7. The process of claim 1, wherein alkyl chloroformate or pivaloyl chloride is used in an amount of 1.0 to 2.0 molar equivalents of compound of Formula III.

8. The process of claim 7, wherein alkyl chloroformate or pivaloyl chloride is used in an amount of 1.1 to 1.5 molar equivalents of compound of Formula III.

9. The process of claim 1, wherein the organic base is used in an amount of 1.0 to 2.0 molar equivalents of the compound of Formula III.

10. The process of claim 9, wherein the organic base is used in an amount of 1.1 to 1.5 molar equivalents of the compound of Formula III.

11. The process of claim 1 wherein the reaction is carried out in the temperature range from about −40° C. to about 10° C.

12. The process according to claim 11 wherein the preferred temperature range being from about −15° C. to about 10° C.

13. The process of claim 1 further comprises suitable aqueous basic work-up after the reaction is complete.

14. The process of claim 13 wherein said work-up is done in the presence of water and a base.

15. The process of claim 14 wherein base is selected from sodium or potassium hydroxide.

16. The process of claim 13 wherein said work-up includes extraction with an organic solvent.

17. The process of claim 16 wherein an organic solvent is water-immiscible or partially miscible with water.

18. The process of claim 17 wherein an organic solvent is selected from chloroform, dichloromethane, 1,2-dichloroethane, hexanes, cyclohexane, toluene, methyl acetate and ethyl acetate.

19. The process of claim 13 further comprises reducing the solvent by evaporation or evaporation under vacuum to give a residue.

20. The process of claim 19 further comprises adding a polar solvent to said residue.

21. The process of claim 20 wherein polar solvent is selected from the group consisting of lower alkanol, ketones or esters and mixture(s) thereof.

22. The process of claim 21 further comprises adding an anti-solvent to effect precipitation.

23. The process of claim 21 wherein the polar solvent is selected from the group consisting of methanol, ethanol, acetone, ethyl acetate and mixture(s) thereof.

24. The process of claim 23 wherein an anti-solvent is at least partially miscible.

25. The process of claim 24 wherein an anti-solvent includes alkane, mixture of alkanes, ether, aromatic hydrocarbon.

26. The process of claim 25 wherein an antisolvent is selected from the group consisting of hexane, cyclohexane, cyclopentane, isopropyl ether, benzene and toluene.

* * * * *

UNITED STATES PATENT AND TRADEMARK OFFICE
CERTIFICATE OF CORRECTION

PATENT NO.   : 6,803,468 B2
DATED        : October 12, 2004
INVENTOR(S)  : Yatendra Kumar et al.

It is certified that error appears in the above-identified patent and that said Letters Patent is hereby corrected as shown below:

Title page,
Item [54], Title, "5-methylnicontinoyl" should read -- 5-methylnicotinoyl --
Item [75], Inventor, "Shallendra" should read -- Shailendra --
Item [56], References Cited, FOREIGN PATENT DOCUMENTS,
"12/1933…..C07D/401/17" should read -- 12/1993…..C07D/401/14 --

Column 3,
Lines 16 and 24, "Formula II" should read -- Formula III --

Signed and Sealed this

First Day of February, 2005

JON W. DUDAS
*Director of the United States Patent and Trademark Office*